US007608436B2

(12) United States Patent
Harrison et al.

(10) Patent No.: US 7,608,436 B2
(45) Date of Patent: Oct. 27, 2009

(54) PROCESS FOR PRODUCING SACCHARIDE OLIGOMERS

(75) Inventors: Michael D. Harrison, Decatur, IL (US); James C. Purdue, West Lafayette, IN (US); Penelope A. Patton, Decatur, IL (US); Andrew J. Hoffman, Mt. Zion, IL (US); James M. Gaddy, Decatur, IL (US); Chi-Li Liu, Decatur, IL (US); Robert V. Schanefelt, Decatur, IL (US)

(73) Assignee: Tate & Lyle Ingredients Americas, Inc., Decatur, IL (US)

( * ) Notice: Subject to any disclaimer, the term of this patent is extended or adjusted under 35 U.S.C. 154(b) by 288 days.

(21) Appl. No.: 11/339,306

(22) Filed: Jan. 25, 2006

(65) Prior Publication Data

US 2007/0172931 A1   Jul. 26, 2007

(51) Int. Cl.
| | | |
|---|---|---|
| C12P 19/02 | (2006.01) | |
| A23L 1/09 | (2006.01) | |
| A23L 1/236 | (2006.01) | |
| C08B 37/00 | (2006.01) | |
| A61K 31/715 | (2006.01) | |

(52) U.S. Cl. .......... 435/105; 424/439; 426/548; 426/658; 426/659; 426/660; 435/94; 435/95; 435/96; 435/97; 435/98; 435/99; 514/54; 514/61; 536/123; 536/123.1

(58) Field of Classification Search .......... None
See application file for complete search history.

(56) References Cited

U.S. PATENT DOCUMENTS

| | | | |
|---|---|---|---|
| 2,613,206 A | 10/1952 | Caldwell | 260/233.5 |
| 2,661,349 A | 12/1953 | Caldwell et al. | 260/224 |
| 3,729,380 A | 4/1973 | Sugimoto et al. | 195/31 R |
| 4,619,831 A | 10/1986 | Sharma | 426/93 |
| 4,626,288 A | 12/1986 | Trzasko et al. | 106/210 |
| 4,937,091 A | 6/1990 | Zallie et al. | 426/582 |
| 5,089,171 A | 2/1992 | Chiu | 252/315.3 |
| 5,139,575 A | 8/1992 | Matsuda et al. | 127/23 |
| 5,281,276 A | 1/1994 | Chiu et al. | 127/65 |
| 5,368,878 A | 11/1994 | Smick et al. | 426/646 |
| 5,372,835 A | 12/1994 | Little et al. | 426/573 |
| 5,376,399 A | 12/1994 | Dreese et al. | 426/658 |
| H1394 H | 1/1995 | Dreese | 426/603 |
| H1395 H | 1/1995 | Prosser | 426/633 |
| 5,378,286 A | 1/1995 | Chiou et al. | 127/36 |
| 5,378,491 A | 1/1995 | Stanley et al. | 426/661 |
| 5,387,426 A | 2/1995 | Harris et al. | 426/573 |
| 5,395,640 A | 3/1995 | Harris et al. | 426/573 |
| 5,409,542 A | 4/1995 | Henley et al. | 127/65 |
| 5,409,726 A * | 4/1995 | Stanley et al. | 426/573 |
| 5,436,019 A | 7/1995 | Harris et al. | 426/573 |
| 5,472,732 A | 12/1995 | Ohkuma et al. | 426/658 |
| 5,496,861 A | 3/1996 | Rouse et al. | 514/778 |
| 5,593,503 A | 1/1997 | Shi et al. | 127/71 |
| 5,651,936 A | 7/1997 | Reed et al. | 420/3 |
| 5,711,986 A | 1/1998 | Chiu et al. | 426/658 |
| 5,714,600 A | 2/1998 | McNaught et al. | 536/102 |
| 5,849,090 A | 12/1998 | Haralampu et al. | 127/65 |
| 5,886,168 A | 3/1999 | Brumm | 536/103 |
| 5,902,410 A | 5/1999 | Chiu et al. | 127/71 |
| 5,904,941 A | 5/1999 | Xu et al. | 426/52 |
| 5,962,047 A | 10/1999 | Gross et al. | 426/48 |
| 6,013,299 A | 1/2000 | Haynes et al. | 426/549 |
| 6,043,229 A | 3/2000 | Kettlitz et al. | 514/60 |
| 6,054,302 A | 4/2000 | Shi et al. | 435/95 |
| 6,090,594 A | 7/2000 | Kettlitz et al. | 435/98 |
| 6,113,976 A | 9/2000 | Chiou et al. | 426/661 |
| 6,274,567 B1 | 8/2001 | Brown et al. | 514/60 |
| 6,299,924 B1 | 10/2001 | Chiu et al. | 426/573 |
| 6,303,174 B1 | 10/2001 | McNaught et al. | 426/549 |
| 6,348,452 B1 | 2/2002 | Brown et al. | 514/60 |
| 6,352,733 B1 | 3/2002 | Haynes et al. | 426/549 |
| 6,423,364 B1 | 7/2002 | Altemueller et al. | 426/634 |
| 6,468,355 B1 | 10/2002 | Thompson et al. | 127/71 |
| 6,528,498 B2 | 3/2003 | Brown et al. | 514/60 |
| 6,613,373 B2 | 9/2003 | Haynes et al. | 426/549 |
| 6,623,943 B2 | 9/2003 | Schmiedel et al. | 435/98 |
| 6,664,389 B1 | 12/2003 | Shi et al. | 536/102 |
| 6,670,155 B2 | 12/2003 | Antrim et al. | 435/95 |

(Continued)

FOREIGN PATENT DOCUMENTS

EP   363741 A2   4/1990

(Continued)

OTHER PUBLICATIONS

Nikolov et al., *Biotechnology and Bioengineering* 34:694-704 (1989).
Bourquelot et al., *Journ de Pharm et de Chim* 7:569-573, 598 (Jun. 16, 1912) (translation attached).
El-Sayed et al., *Acta Alimentaria* 23:43-58 (1994).
Sievert et al., *Cereal Chemistry* 66:342-347 (1989).
Sievert et al., *Cereal Chemistry* 67:217-221(1990).

(Continued)

*Primary Examiner*—Herbert J. Lilling
(74) *Attorney, Agent, or Firm*—Williams, Morgan & Amerson, P.C.

(57) ABSTRACT

A process for preparing saccharide oligomers uses an aqueous feed composition that comprises at least one monosaccharide or linear saccharide oligomer, and has a solids concentration of at least about 70% by weight. The feed composition is heated to a temperature of at least about 40° C., and is contacted with at least one catalyst that accelerates the rate of cleavage or formation of glucosyl bonds, such as enzyme or acid, for a time sufficient to cause formation of non-linear saccharide oligomers. A product composition is produced that contains a higher concentration of non-linear saccharide oligomers than linear saccharide oligomers.

36 Claims, 8 Drawing Sheets

U.S. PATENT DOCUMENTS

| | | |
|---|---|---|
| 6,844,172 B2 | 1/2005 | Bergsma et al. ............... 435/98 |
| 6,890,571 B2 | 5/2005 | Shi et al. ..................... 426/28 |
| 6,896,915 B2 | 5/2005 | Shi et al. ..................... 426/20 |
| 6,927,048 B2 | 8/2005 | Verser et al. ................ 435/161 |
| 6,929,815 B2 * | 8/2005 | Bengs et al. ................ 426/578 |
| 6,929,817 B2 | 8/2005 | Shi et al. .................... 426/661 |
| 7,081,261 B2 | 7/2006 | Shi et al. ..................... 426/28 |
| 2002/0162138 A1 | 10/2002 | Kossmann et al. .......... 800/284 |
| 2002/0192291 A1 | 12/2002 | Bergsma et al. ............. 424/488 |
| 2003/0045504 A1 | 3/2003 | Brown et al. ................. 514/60 |
| 2003/0054501 A1 | 3/2003 | Schmiedel et al. .......... 435/101 |
| 2003/0134394 A1 | 7/2003 | Antrim et al. ................ 435/95 |
| 2003/0215499 A1 | 11/2003 | Shi et al. ..................... 424/465 |
| 2003/0215561 A1 | 11/2003 | Shi et al. .................... 426/661 |
| 2003/0215562 A1 | 11/2003 | Shi et al. .................... 426/661 |
| 2003/0219520 A1 | 11/2003 | Shi et al. .................... 426/549 |
| 2004/0092732 A1 | 5/2004 | Antrim et al. .......... 536/123.13 |
| 2005/0095350 A1 | 5/2005 | Barresi et al. ............... 426/658 |

FOREIGN PATENT DOCUMENTS

| | | |
|---|---|---|
| EP | 486936 A1 | 5/1992 |
| EP | 487000 A1 | 5/1992 |
| EP | 499648 B1 | 8/1992 |
| EP | 529893 A1 | 3/1993 |
| EP | 529894 A1 | 3/1993 |
| EP | 553368 A1 | 8/1993 |
| EP | 688872 A1 | 12/1995 |
| EP | 806434 A1 | 11/1997 |
| EP | 0 884 384 | 12/1998 |
| EP | 1 088 832 | 4/2001 |
| EP | 0 846 704 | 3/2002 |
| EP | 1 362 869 | 11/2003 |
| EP | 1 382 687 A1 | 1/2004 |
| JP | 60030695 | 2/1985 |
| JP | 61124389 | 6/1986 |
| JP | 61212296 | 9/1986 |
| JP | 61219392 | 9/1986 |
| JP | 63109791 | 5/1988 |
| JP | 03175989 | 7/1991 |
| JP | 04290809 A | 10/1992 |
| JP | 10080294 A | 3/1998 |
| JP | 10191931 A | 7/1998 |
| JP | 11196762 | 7/1999 |
| JP | 231469 A | 8/2001 |
| WO | WO91/07106 | 5/1991 |
| WO | WO93/03629 | 3/1993 |
| WO | WO96/08261 | 3/1996 |
| WO | WO96/09815 | 4/1996 |
| WO | WO98/15347 | 4/1998 |
| WO | WO00/14249 | 3/2000 |
| WO | WO2005/040223 | 5/2005 |
| WO | WO2006/041563 | 4/2006 |

* cited by examiner

Changes in Sugar Distributions in 1300 Syrup due to Enzyme or Acid.
Enzyme was 0.13% v/v Spirizyme glucoamylase; acid was H2SO4 at pH 2.3, temp was 60C

PROCESS FOR PRODUCING SACCHARIDE OLIGOMERS

BACKGROUND OF THE INVENTION

A variety of carbohydrates are used in food products, such as various sugars and starches. Many of these carbohydrates are digested in the human stomach and small intestine. Dietary fiber in food products, in contrast, is generally not digested in the stomach or small intestine, but is potentially fermentable by microorganisms in the large intestine.

There is an interest in developing ingredients that are suitable for use in food products and that are either non-digestible or only digestible to a limited extent, in order to enhance the dietary fiber content or reduce the caloric content of the food. These modifications have certain health benefits.

There is a need for edible materials which have a reduced content of easily digestible carbohydrates, and which can be used in place of, or in addition to, conventional carbohydrate products in foods.

SUMMARY OF THE INVENTION

One aspect of the invention is a process for preparing saccharide oligomers. The process uses an aqueous feed composition that comprises at least one monosaccharide or linear saccharide oligomer, and that has a solids concentration of at least about 70% by weight. The feed composition is heated to a temperature of at least about 40° C., and is contacted with at least one catalyst that accelerates the rate of cleavage or formation of glucosyl bonds for a time sufficient to cause formation of non-linear saccharide oligomers. A product composition is produced that contains a higher concentration of non-linear saccharide oligomers than linear saccharide oligomers.

In one embodiment of the process, the at least one catalyst is an enzyme that accelerates the rate of cleavage or formation of glucosyl bonds. In another embodiment of the process, the at least one catalyst is an acid. In some embodiments of the process, acid and enzyme can be used in sequence, with the feed composition first being treated with enzyme and subsequently with acid, or vice versa.

Another aspect of the invention is a carbohydrate composition that comprises a major amount on a dry solids basis (i.e., greater than 50% by weight on a dry solids basis) of linear and non-linear saccharide oligomers, wherein the concentration of non-linear saccharide oligomers is greater than the concentration of linear saccharide oligomers. In some embodiments of the invention, the concentration of non-linear saccharide oligomers in the composition is at least twice as high as the concentration of linear saccharide oligomers.

Another aspect of the invention is a food product that comprises a carbohydrate composition as described above. The food product can be, for example, a bread, cake, cookie, cracker, extruded snack, soup, frozen dessert, fried food, pasta product, potato product, rice product, corn product, wheat product, dairy product, yogurt, confectionary, hard candy, nutritional bar, breakfast cereal, or beverage.

DESCRIPTION OF ILLUSTRATIVE EMBODIMENTS

Figure 1:
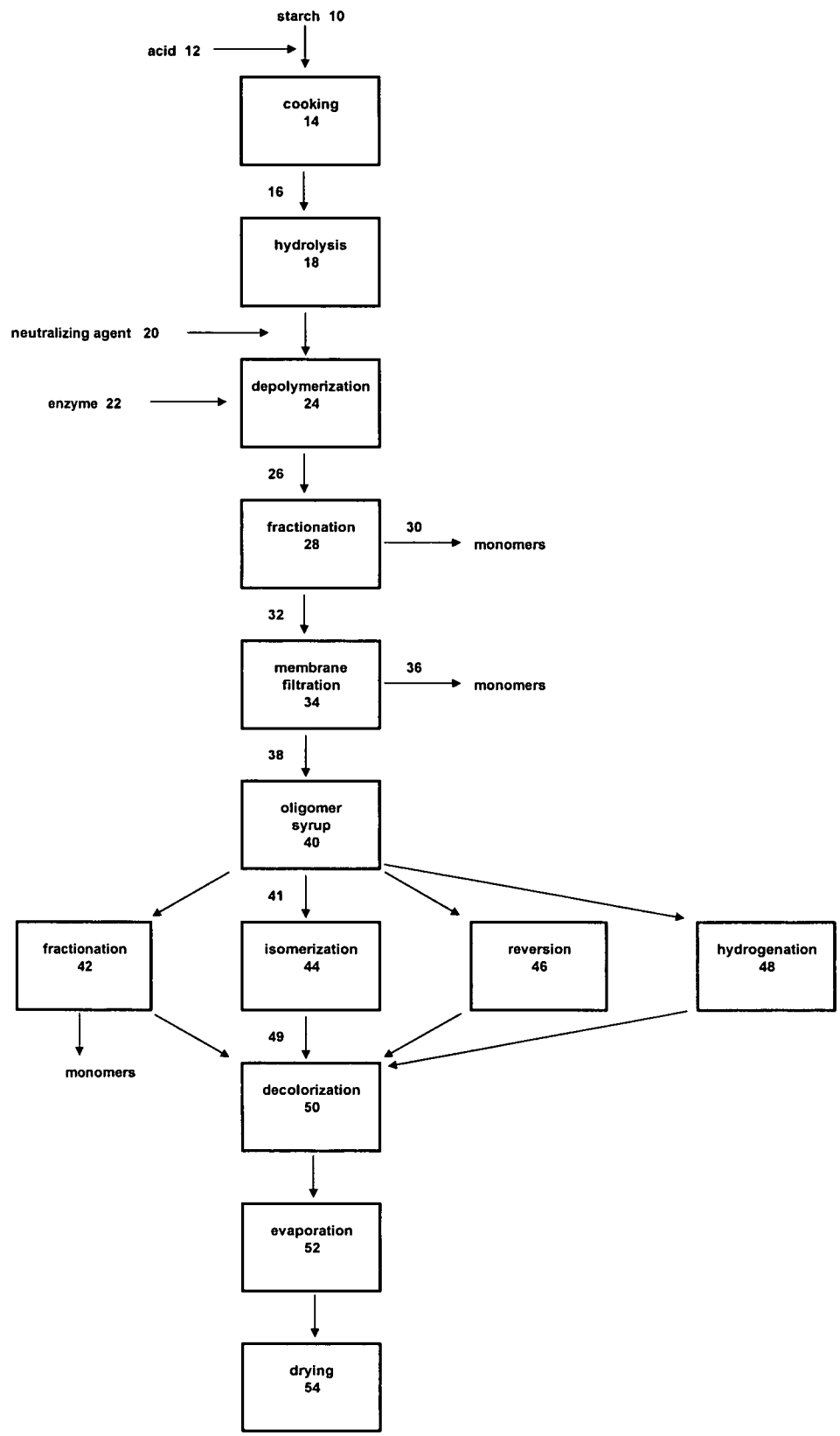
FIG. 1 is process flow diagram of one embodiment of the present invention.

One aspect of the present invention is a process for making a slowly digestible saccharide oligomer composition that is suitable for use in foods. "Slowly digestible" as the term is used herein means that one or more carbohydrates are either not digested at all in the human stomach and small intestine, or are only digested to a limited extent.

Both in vitro and in vivo tests can be performed to estimate the rate and extent of carbohydrate digestion in humans. The "Englyst Assay" is an in vitro enzyme test that can be used to estimate the amounts of a carbohydrate ingredient that are rapidly digestible, slowly digestible or resistant to digestion (European Journal of Clinical Nutrition (1992) Volume 46 (Suppl. 2), pages S33-S50). Thus, any reference herein to "at least about 50% by weight on a dry solids basis" of a material being "slowly digestible" means that the sum of the percentages of that material that are classified as slowly digestible or as resistant by the Englyst assay totals at least about 50%.

It should be understood that the term "food" is used in a broad sense herein to include a variety of substances that can be ingested by humans, such as beverages and medicinal capsules or tablets.

The terms "oligosaccharides" and "saccharide oligomers" are used herein to refer to saccharides comprising at least two saccharide units, for example saccharides having a degree of polymerization ("DP") of about 2-30. For example, a disaccharide has a DP of 2.

In some embodiments of the invention, the aqueous feed composition includes at least one monosaccharide and at least one linear saccharide oligomer, and may contain several of each. In many cases, monosaccharides and oligosaccharides will make up at least about 70% by weight on a dry solids basis of the feed composition. It is generally helpful for the starting material to have as high a concentration of monosaccharides as possible, in order to maximize the yield of the desired oligomers. A high solids concentration tends to drive the equilibrium from hydrolysis toward condensation (reversion), thereby producing higher molecular weight products. Therefore the water content of the starting material is preferably relatively low. For example, in certain embodiments, the feed composition comprises at least about 75% dry solids by weight. ("Dry solids" is sometimes abbreviated herein as "ds.") In some cases, the feed composition comprises about 75-90% solids by weight, which will generally give the appearance of a viscous syrup or damp powder at room temperature.

Examples of suitable starting materials include, but are not limited to, syrups made by hydrolysis of starch, such as dextrose greens syrup (i.e., recycle stream of mother liquor from dextrose monohydrate crystallization), other dextrose syrups, corn syrup, and solutions of maltodextrin.

If the feed composition comprises maltodextrin, the process optionally can also include the steps of hydrolyzing the maltodextrin to form a hydrolyzed saccharide solution and concentrating the hydrolyzed saccharide solution to at least about 70% dry solids to form the feed composition. The concentrating and the contacting of the feed with the catalyst can occur simultaneously, or the concentrating can occur prior to contacting the feed composition with the catalyst.

The feed composition is contacted with the at least one catalyst for a period of time that can vary. In some cases, the contacting period will be at least about five hours. In some embodiments of the invention, the feed composition is contacted with the at least one catalyst for about 15-100 hours. In other embodiments, shorter contacting times can be used with higher temperatures, in some cases even less than one hour.

In one embodiment of the invention, enzymatic reversion is used to produce nonlinear oligosaccharides. The enzyme can be, for example, one that accelerates the rate of cleavage of alpha 1-2, 1-3, 1-4, or 1-6 glucosyl bonds to form dextrose residues. One suitable example is a glucoamylase enzyme composition, such as a commercial enzyme composition that is denominated as a glucoamylase. It should be understood that such a composition can contain some quantity of enzymes other than pure glucoamylase, and it should not be assumed that it is in fact glucoamylase itself that catalyzes the desired production of nonlinear oligosaccharides.

Therefore, the feed composition can be contacted with glucoamylase or any other enzyme that acts on dextrose polymers. The amount of enzyme can suitably be about 0.5-2.5% by volume of the feed composition. In some embodiments of the process, the feed composition is maintained at about 55-75° C. during the contacting with the enzyme, or in some cases about 60-65° C. At this temperature, depending on the water content, the material will become a liquid, or a mixture of liquid and solid. Optionally, the reaction mixture can be mixed or agitated to distribute the enzyme. The reaction mixture is maintained at the desired temperature for the time necessary to achieve the desired degree of reversion to nonlinear oligomers. In some embodiments of the process, the feed composition is contacted with the enzyme for about 20-100 hours prior to inactivation of the enzyme, or in some cases, for about 50-100 hours prior to inactivation. Techniques for inactivating glucoamylase are well known in the field. Alternatively, instead of inactivating the enzyme, it can be separated by membrane filtration and recycled.

The resulting composition has a high concentration of non-linear oligosaccharides, such as isomaltose. This product composition contains a higher concentration of non-linear saccharide oligomers than linear saccharide oligomers. In some cases, the concentration of non-linear saccharide oligomers in the final composition is at least twice as high as the concentration of linear saccharide oligomers.

Gastrointestinal enzymes readily recognize and digest carbohydrates in which the dextrose units are linked alpha (1–>4) ("linear" linkages). Replacing these linkages with alternative linkages (alpha (1–>3), alpha (1–>6) ("non-linear" linkages) or beta linkages, for example) greatly reduces the ability of gastrointestinal enzymes to digest the carbohydrate. This will allow the carbohydrates to pass on into the small intestines largely unchanged.

In some cases, the product composition comprises a minor amount (i.e., less than 50 wt % on a dry solids basis, and usually a much lower concentration) of residual monosaccharides. The process can include the additional step of removing at least some of the residual monosaccharides (and optionally other species as well) from the product composition by membrane filtration, chromatographic fractionation, or digestion via fermentation. The separated monosaccharides can be combined with other process streams, for example for production of dextrose or corn syrup. Alternatively, the separated monosaccharides can be recycled into the feed composition.

Another embodiment of the invention is a process that involves acid reversion of monosaccharides. The starting material is the same as described above with respect to the enzyme version of the process. A variety of acids can be used, such as hydrochloric acid, sulfuric acid, phosphoric acid, or a combination thereof. In some embodiments of the process, acid is added to the feed composition in an amount sufficient to make the pH of the feed composition no greater than about 4, or in some cases, in an amount sufficient to make the pH of the feed composition about 1.0-2.5, or about 1.5-2.0. In some embodiments, the solids concentration of the feed composition is about 70-90%, the amount of acid added to the feed is about 0.05%-0.25% (w/w) acid solids on syrup dry solids, and the feed composition is maintained at a temperature of about 70-90° C. during the contacting with the acid. As in the enzyme version of the process, the reaction conditions are maintained for a time sufficient to produce the desired oligomers, which in some embodiments of the process will be about 4-24 hours.

In one particular embodiment, the solids concentration of the feed composition is at least about 80% by weight, acid is added to the feed composition in an amount sufficient to make the pH of the composition about 1.8, and the feed composition is maintained at a temperature of at least about 80° C. for about 4-24 hours after it is contacted with the acid.

In another particular embodiment, the solids concentration of the feed composition is about 90-100% by weight, and the feed composition is maintained at a temperature of at least about 149° C. (300° F.) for about 0.1-15 minutes after it is contacted with the acid. The acid used to treat the feed can be a combination of phosphoric acid and hydrochloric acid (at the same concentrations discussed above). In one particular embodiment, the contacting of the feed composition with the acid takes place in a continuous pipe/flow through reactor.

By far the most plentiful glycosidic linkage in starch is the alpha-1,4 linkage, and this is the linkage most commonly broken during acid hydrolysis of starch. But acid-catalyzed reversion (condensation) can take place between any two hydroxyl groups, and, given the large variety of combinations and geometries available, the probability of an alpha-1,4 linkage being formed is relatively small. The human digestive system contains alpha amylases which readily digest the alpha-1,4 linkages of starch and corn syrups. Replacing these linkages with linkages unrecognized by enzymes in the digestive system will allow the product to pass through to the small intestines largely unchanged.

The saccharide distributions resulting from acid treatment are believed to be somewhat different than from enzyme treatment. It is believed that these acid-catalyzed condensation products will be less recognizable by the enzymes in the human gut than enzyme-produced products, and therefore less digestible.

The acid treatment progresses differently than enzyme treatment. Enzymes rapidly hydrolyze linear oligomers and slowly form non-linear oligomers, whereas with acid the reduction in linear oligomers and the increase in non-linear oligomers occur at comparable rates. Dextrose is formed rapidly by enzymatic hydrolysis of oligomers, and consumed slowly as non-linear condensation products are formed, whereas with acid dextrose concentrations increase slowly.

Optionally, enzymatic or acid reversion can be followed by hydrogenation. The hydrogenated product should have lower caloric content than currently available hydrogenated starch hydrolysates. In one embodiment, the hydrogenation can be used to decolorize the product composition without substantially changing its dextrose equivalence (DE).

In one version of the process, enzyme and acid can be used sequentially, in any order. For example, the at least one catalyst used in the first treatment can be enzyme, and the product composition can be subsequently contacted with an acid that accelerates the rate of cleavage or formation of glucosyl bonds. Alternatively, the at least one catalyst used in the first treatment can be acid, and the product composition can be subsequently contacted with an enzyme that accelerates the rate of cleavage or formation of glucosyl bonds.

The product composition produced by the treatment with acid, enzyme, or both, has an increased concentration on a dry solids basis of non-linear saccharide oligomers. In some cases, the concentration of non-linear saccharide oligomers having a degree of polymerization of at least three (DP3+) in the product composition is at least about 20%, at least about 25%, at least about 30%, or at least about 50% by weight on a dry solids basis. In some embodiments, the concentration of non-linear saccharide oligomers in the product composition is at least twice as high as the concentration of linear saccharide oligomers.

In one particular embodiment, the concentration of non-linear saccharide oligomers in the product composition is at least about 90% by weight on a dry solids basis, and the concentration of isomaltose is at least about 70% by weight on a dry solids basis.

The product composition will often contain some quantity (typically less than 50% by weight on a dry solids basis, and often much less) of residual monosaccharides. Optionally, at least some of the residual monosaccharides (and other species) can be separated from the oligomers (for example by membrane filtration, chromatographic separation, or digestion via fermentation) and the monosaccharide stream can be recycled into the process feed. In this way, simple sugar syrups can be converted to high-value food additives.

The oligomer-rich syrup produced by the processes described herein can be used in foods to increase dietary fiber. The syrup contains naturally-occurring oligosaccharides that have both low viscosity and low glycemic index. Many of these oligomers will comprise at least one non-alpha-1,4 linkage. They should be highly fermentable in the large intestine, which give them added health benefits as prebiotics. In some embodiments of the invention, at least about 50% by weight on a dry solids basis of the product composition is slowly digestible.

The beneficial effects of oligosaccharides as dietary fiber have been well documented. Sugar oligomers that resist digestion in the small intestine but are fermentable in the large intestine have been shown to have several beneficial effects, such as reducing cholesterol, attenuating blood dextrose, and maintaining gastrointestinal health.

FIG. 1 shows one embodiment of a process which can make use of the reversion technique described above. The process can begin with a starch, for example a vegetable starch. Conventional corn starch is one suitable example. The process will generally operate more efficiently if the beginning starch has a relatively high purity. In one embodiment, the high purity starch contains less than 0.5% protein on a dry solids basis. Although some of the following discussion focuses on corn, it should be understood that the present invention is also applicable to starches derived from other sources, such as potato and wheat, among others.

As shown in FIG. 1, the starch 10 can have acid 12 added to it and can then be gelatinized 14 in a starch cooker, for example in a jet cooker in which starch granules are contacted with steam. In one version of the process, the starch slurry, adjusted to a pH target of 3.5 by addition of sulfuric acid, is rapidly mixed with steam in a jet cooker and held at 149 to 152° C. (300 to 305° F.) for 4 minutes in a tail line. The gelatinized starch 16 is hydrolyzed 18 by exposure to acid at high temperature during jet cooking. The hydrolysis reduces the molecular weight of the starch and generates an increased percentage of monosaccharides and oligosaccharides in the composition. (As mentioned above, the term "oligosaccharides" is used herein to refer to saccharides comprising at least two saccharide units, for example saccharides having a degree of polymerization (DP) of about 2-30.) A neutralizing agent 20, such as sodium carbonate, can be added to stop the acid hydrolysis, and then the composition can be further depolymerized 24 by contacting it with a hydrolytic enzyme 22. Suitable enzymes include alpha amylases such as Termamyl, which is available from Novozymes. This enzymatic hydrolysis further increases the percentage of monosaccharides and oligosaccharides present in the composition. The overall result of the hydrolysis by acid and enzyme treatment is to saccharify the starch. The saccharified composition can be isomerized to change the monosaccharide profile, for example to increase the concentration of fructose.

The saccharified composition 26 can then be purified, for example by chromatographic fractionation 28. In one embodiment that employs a sequential simulated moving bed (SSMB) chromatography procedure, a solution of mixed saccharides is pumped through a column filled with resin beads. Depending on the chemical nature of the resin, some of the saccharides interact with the resin more strongly leading to a retarded flow through the resin compared to saccharides that interact with the resin more weakly. This fractionation can produce one stream 30 that has a high content of monosaccharides, such as dextrose and fructose. High fructose corn syrup is an example of such a stream. The fractionation also produces a raffinate stream 32 (i.e., faster moving components through the resin bed) that has a relatively high concentration of oligosaccharides (e.g., about 5-15% oligosaccharides on a dry solids basis (d.s.b.)) and also contains a smaller concentration of monosaccharides such as dextrose and fructose. Although the term "stream" is used herein to describe certain parts of the process, it should be understood that the process of the present invention is not limited to continuous operation. The process can also be performed in batch or semi-batch mode.

The raffinate 32 can be further fractionated by membrane filtration 34, for example by nanofiltration, optionally with diafiltration. For example, these filtration steps can be performed using a Desal DK spiral wound nanofiltration cartridge at about 500 psi of pressure and at 40-60 degrees centigrade temperature. The fractionation described in step 34 could also be accomplished by sequential simulated moving bed chromatography (SSMB). The membrane filtration produces a permeate 36 (i.e., components that pass through the membrane) which comprises primarily monosaccharides, and a retentate 38 (i.e., components rejected by the membrane) which comprises primarily oligosaccharides. ("Primarily" as used herein means that the composition contains more of the listed component than of any other component on a dry solids basis.) The permeate 36 can be combined with the monomer stream 30 (e.g., high fructose corn syrup). The permeate is a monosaccharide-rich stream and the retentate is an oligosaccharide-rich stream. In other words, the nanofiltration concentrates the oligosaccharides in the retentate and the monosaccharides in the permeate, relative to the nanofiltration feed.

The retentate 38, which can be described as an oligosaccharide syrup 40, can have a sufficiently high content of oligosaccharides that are slowly digestible (e.g., at least about 50% by weight d.s.b., or in some cases at least about 90%) so that it can be dried or simply evaporated to a concentrated syrup and used as an ingredient in foods. However, in many cases, it will be useful to further process and purify this composition. Such purification can include one or more of the following steps. (Although FIG. 1 shows four such purification steps 42, 44, 46, and 48 as alternatives, it should be understood that two or more of these steps could be used in the process.)

The oligomers syrup 40 can be subjected to another fractionation 42, such as a membrane filtration, for example a second nanofiltration, in order to remove at least some of the residual monosaccharides, such as fructose and dextrose. Suitable nanofiltration conditions and equipment are as described above. This nanofiltration produces a permeate, which is a second monosaccharide-rich stream, which can be combined with the monomer stream 30. Alternatively, the further fractionation 42 could be done by chromatographic separation, for example, by simulated mixed-bed chromatography.

The syrup 41 can be isomerized 44 by contacting it with an enzyme such as dextrose isomerase. This will convert at least some of the residual dextrose present into fructose, which may be more valuable in certain situations.

The syrup can be treated with an enzyme or acid to cause reversion or repolymerization 46, in which at least some of the monosaccharides that are still present are covalently bonded to other monosaccharides or to oligosaccharides, thereby reducing the residual monomer content of the syrup even further. Suitable enzymes for use in this step include glucosidases, such as amylase, glucoamylase, transglucosidase, and pullulanase. Cellulase enzymes may produce valuable reversion products for some applications.

The syrup can be hydrogenated 48 to convert at least some of any residual monosaccharides to the corresponding alcohols (e.g., to convert dextrose to sorbitol). When hydrogenation is included in the process, it will typically (but not necessarily) be the final purification step.

The purified oligomer syrup 49 produced by one or more of the above purification steps can then be decolorized 50. Decolorization can be done by treatment with activated carbon followed by microfiltration, for example. In continuous flow systems, syrup streams can be pumped through columns filled with granular activated carbon to achieve decolorization. The decolorized oligomer syrup can then be evaporated 52, for example to about greater than about 70% dry solids (d.s.), giving a product that comprises a high content of oligosaccharides (e.g., greater than 90% by wt d.s.b., and in some instances greater than 95%), and a correspondingly low monosaccharide content. The product comprises a plurality of saccharides which are slowly or incompletely digested by humans, if not totally indigestible. These sugars can include isomaltose, panose and branched oligomers having a degree of polymerization of four or greater.

The process conditions can be modified to recover the majority of the maltose in the feed either in the monomer-rich streams (30, 36) or in the oligomer product stream. For example, a nanofiltration membrane with a slightly larger pores, such as Desal DL, operating at less than 500 psi pressure can be used to increase the amount of maltose in monomer-rich streams.

The oligosaccharide-containing syrup produced by the process can be added to foods as a replacement for, or in addition to, conventional carbohydrates. Thus, another aspect of the invention is a food product that comprising a carbohydrate composition that comprises a major amount on a dry solids basis of linear and non-linear saccharide oligomers, wherein the concentration of non-linear saccharide oligomers is greater than the concentration of linear saccharide oligomers. Specific examples of foods in which the syrup can be used include processed foods such as bread, cakes, cookies, crackers, extruded snacks, soups, frozen desserts, fried foods, pasta products, potato products, rice products, corn products, wheat products, dairy products, yogurts, confectioneries, hard candies, nutritional bars, breakfast cereals, and beverages. A food product containing the oligosaccharide syrup will have a lower glycemic response, lower glycemic index, and lower glycemic load than a similar food product in which a conventional carbohydrate, such as corn starch, is used. Further, because at least some of the oligosaccharides are either only digested to a very limited extent or are not digested at all in the human stomach or small intestine, the caloric content of the food product is reduced. The syrup is also a source of soluble dietary fiber.

Certain embodiments of the invention can be further understood from the following examples.

EXAMPLE 1

Preparation of Non-Linear Oligomers from Dextrose by Enzyme

Concentrated dextrose syrups having solids concentrations of 74%, 79.5%, and 80% were prepared by (1) evaporating diluted syrup or (2) adding water to dextrose powder. Each dextrose/water mixture was placed in a suitable container and heated to 60° C. in a water bath.

Glucoamylase enzyme (Dextrozyme or Spirizyme, from Novozymes A/S) was added to the syrup—approximately 400 µl enzyme to 30 ml syrup. The syrup container was capped, and then shaken vigorously to distribute the enzyme. The syrup was returned to the 60° C. water bath.

The change in sugar distribution was monitored over time by transferring 2-4 ml syrup to a small glass vial, and heating it in a heated block to approximately 85-90° C. to deactivate the enzyme.

The concentration of various sugar species was determined by High Performance Anion Exchange with Pulsed Amperometric Detection, (HPAE-PAD). A Dionex ion chromatograph, DX500, equipped with electrochemical detector and gradient pump, was used for the analyses. The sugars were separated on Dionex Carbopac PA1 analytical and guard columns with gradient delivery of a sodium hydroxide and sodium acetate eluent. The sugars were detected using a gold electrode with a four-potential waveform. Samples were diluted with water and passed through Amicon Ultra-4 centrifugal filter devices before analysis.

Figure 2:
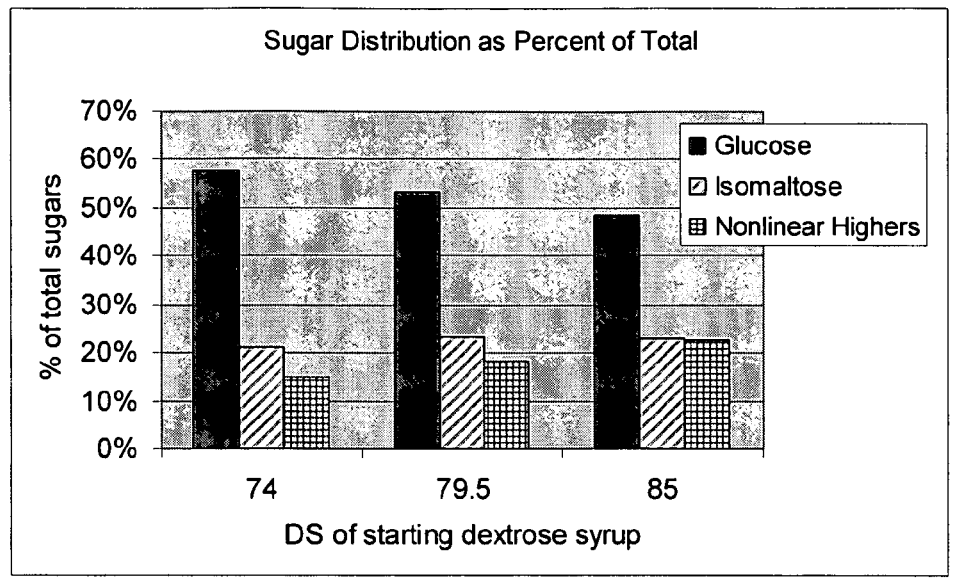
FIG. 2 is a graph of the distribution of certain saccharides in three dextrose compositions used in Example 1.

FIG. 2 illustrates the relative amounts of dextrose, isomaltose and "non-linear highers" (which in this figure refers to nonlinear oligomers having a degree of polymerization of four or more) in syrups of three different initial dextrose compositions treated with 1.3% vol/vol Dextrazyme, a commercial glucoamylase enzyme from Novozymes, for 48 hrs at 60° C. As syrup concentration increased, the amount of monomeric dextrose, relative to other sugars, decreased, and the amount of non-linear higher oligomers increases.

EXAMPLE 2

Preparation of Oligomer Syrup from Corn Syrups

Starting substrates were obtained having a range of extents of conversion, from dextrose greens (95% dextrose) to lightly converted Staley 200 syrup (26 DE, 5% dextrose) and including high (34%) maltose syrup, Neto 7300. The specific products used as starting materials in this example were Staley® 200, Staley® 300, Stale® 1300, Neto® 7300, and Sweetose® 4300 corn syrups, and Staleydex® 3370 dextrose. Some of the characteristics of these materials are given in Table 1.

TABLE 1

Characteristics of starting syrups

|  | Staley 200 | Staley 300 | Staley 1300 | Neto 7300 | Sweetose 4300 | Staleydex 3370 |
|---|---|---|---|---|---|---|
| Degree of conversion | very low | low | regular | regular | high | high |
| Type of conversion | acid-enzyme | acid | acid | acid-enzyme | acid-enzyme | acid-enzyme |
| Dextrose equivalent (D.E.) % | 26 | 35 | 43 | 42 | 63 | 95 |
| % dextrose | 5 | 13 | 19 | 9 | 37 | 90 |
| % maltose | 8 | 10 | 14 | 34 | 29 | 4 |
| % maltotriose | 11 | 11 | 13 | 24 | 9 | 2 |
| % higher saccharides | 76 | 66 | 54 | 33 | 25 | — |

Figure 3:
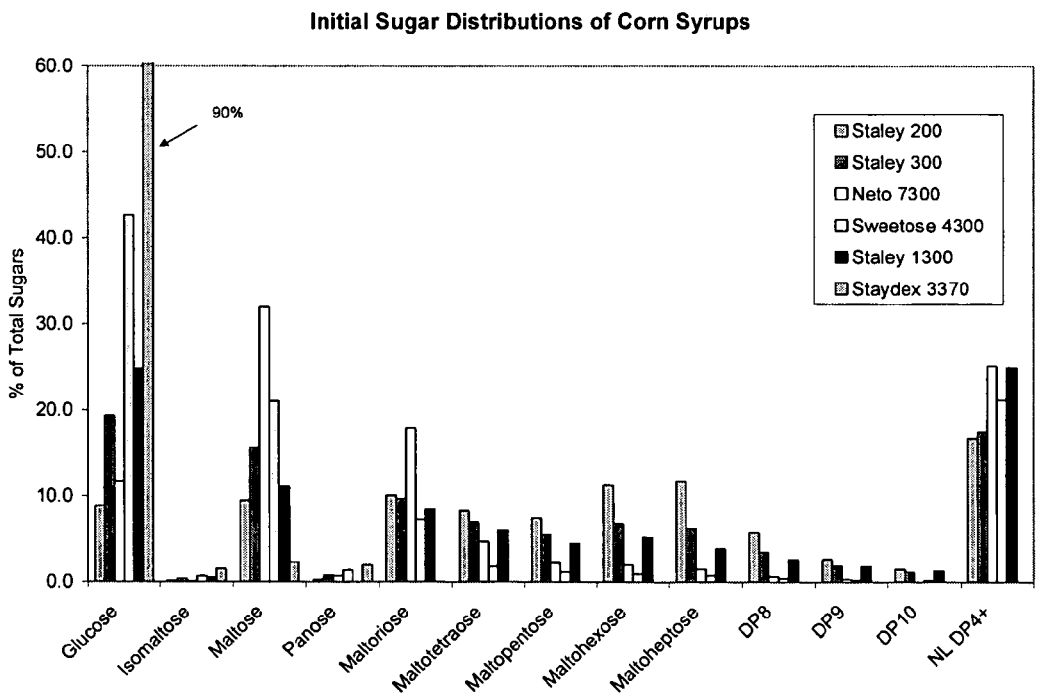
FIG. 3 is a graph of the distribution of certain saccharides in the starting materials used in Example 2.

While many of the less-converted syrups have substantial quantities of nonlinear higher oligomers having a degree of polymerization of four or more (NL DP 4+), they also have substantial quantities of linear oligomers. Several of these syrups contain measurable linear oligomers up through DP 17. FIG. 3 shows the initial saccharide distributions.

The enzymes used were Spirizyme Plus FG and Dextrozyme DX 1.5X glucoamylases and Promozyme D2 pullulanase (supplied by Novozymes), CG 220 Cellulase and Transglucosidase L-500 (supplied by Genencor), Glucoamylase GA150 (supplied by Sunson Industry Group), and Transglucosidase L (supplied by Bio-Cat Inc.).

Figure 4:
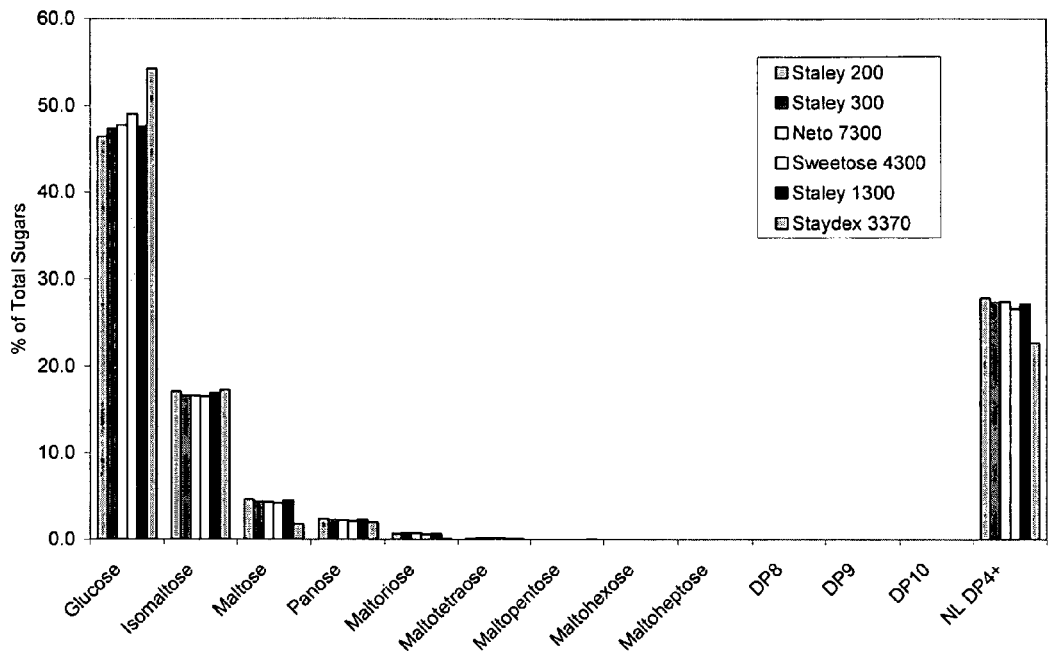
FIG. 4 is a graph of the distribution of certain saccharides in the products prepared by enzyme treatment in Example 2.

The various corn syrups were adjusted to approximately 70% ds. Approximately 3.3% (v/v) Spirizyme Plus FG Enzyme was added to each in 50 ml tubes. The syrups were heated in 60° C. water baths for approximately 4 days. The enzyme was deactivated by heating the syrups to approximately 85° C. for 10 min. FIG. 4 shows the final saccharide distributions. All the syrups reached a comparable sugar distribution by the end of the four day treatment. After reversion, very little linear oligomers remained, and non-linear oligomer content had increased.

Several points should be noted. First, the reverted Staleydex 3370 syrup has a somewhat higher dextrose content and lower content of non-linear oligomers than the other syrups. While all syrups were adjusted to approximately 70% ds before reversion, the less converted syrups, with low initial dextrose content, consumed water as the new distribution was established, and final concentrations were 4-9 percentage points higher than the reverted 3370 syrup. (The hydrolysis of a single DP6 oligomer of dextrose to six dextrose molecules, for example, consumes five water molecules.) As Table 2 shows, the water contents of the reverted syrups trend with the dextrose content, and trend inversely with the higher oligomer content.

TABLE 2

|  | Concentrations After Reversion, % | | |
|---|---|---|---|
| Starting Syrup | Water | Dextrose | NL DP4+ |
| Staydex 3370 | 28 | 54 | 23 |
| Sweetose 4300 | 25 | 49 | 27 |
| Neto 7300 | 21 | 48 | 27 |
| Staley 1300 | 24 | 48 | 27 |
| Staley 300 | 19 | 47 | 27 |
| Staley 200 | 20 | 46 | 28 |

Lower water content drives the equilibrium toward a higher concentration of reversion products. If the water content had been adjusted so that final water contents had been identical, we believe the sugar distributions would also have been identical.

Second, all syrups after reversion had much higher percentages of branched oligomers at each degree of polymerization (DP) than linear oligomers. Compare the relative amount of maltose vs. isomaltose, panose vs. maltotriose, and NL DP4+ vs. linear oligomers of DP4 and greater (of which there is virtually none remaining after reversion).

Figure 5:
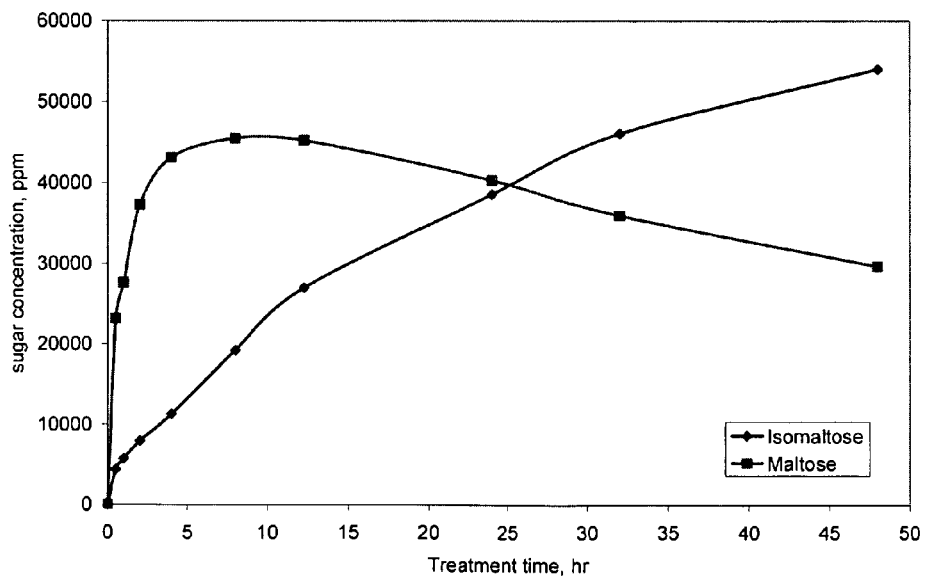
FIG. 5 is a graph of the change over time in maltose and isomaltose concentrations when a composition was treated with enzyme in Example 2.

FIG. 5 shows the change in maltose and isomaltose concentrations over time when a concentrated dextrose syrup was treated with Spirizyme. It would appear that linear oligomers are the kinetic products while non-linear oligomers are the thermodynamic products. That is, forming the linear dimer, maltose, from dextrose is a rapid and reversible reaction with low activation energy. Forming the non-linear dimer, isomaltose, is a slower reaction, and its reverse reaction has a high activation energy.

Figure 6:
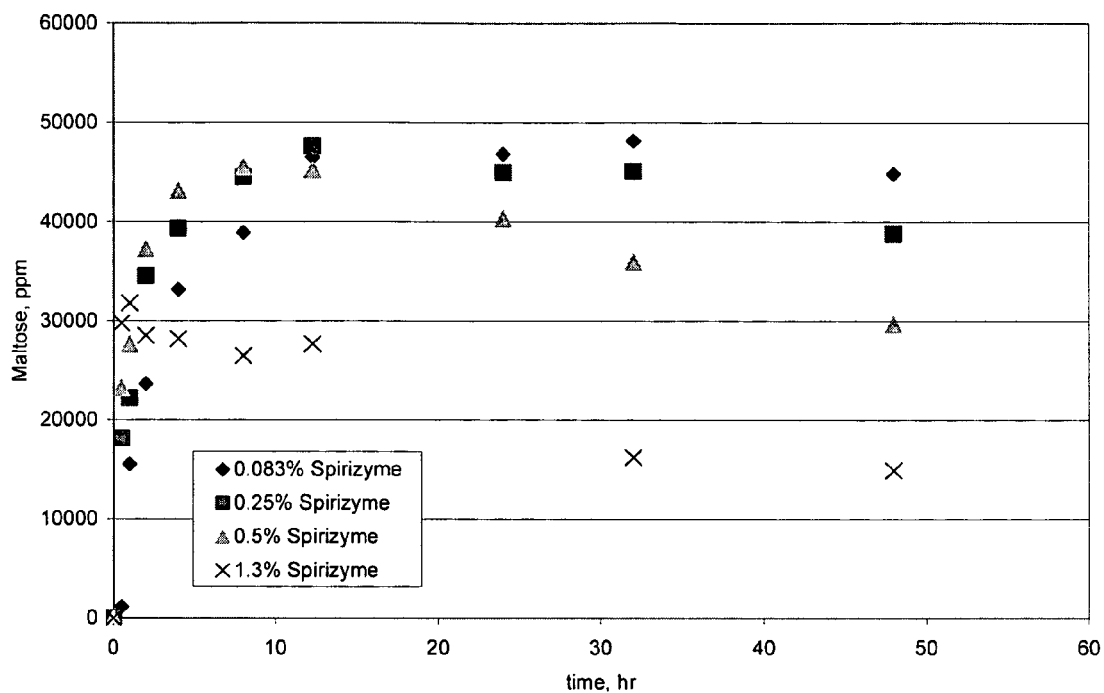
FIG. 6 is a graph of the change in maltose concentration and FIG. 7 is a graph of the change in isomaltose concentration when dextrose syrup was treated with different concentrations of enzyme in Example 2.
Figure 7:
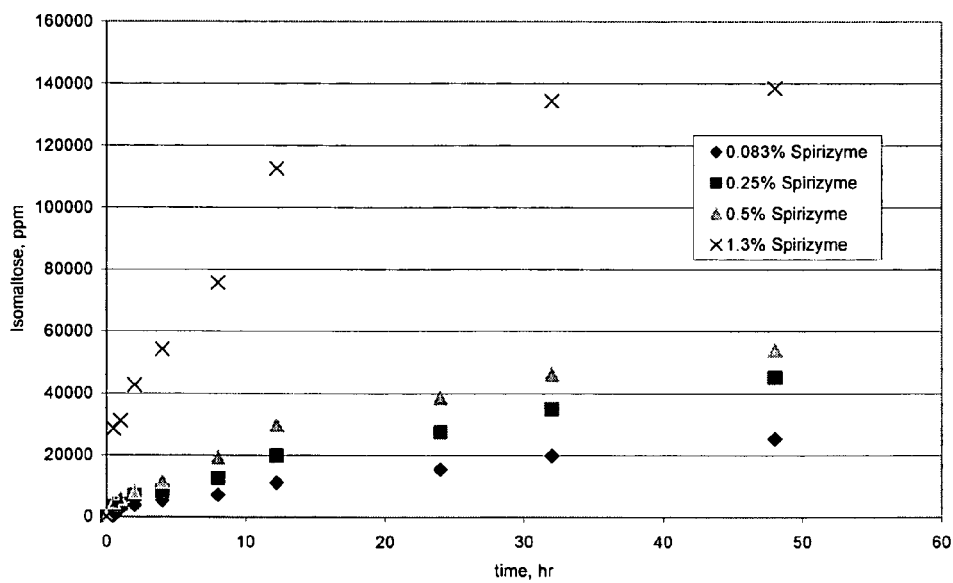

FIGS. 6 and 7 show the change in maltose and isomaltose concentrations over time when 70% dextrose syrup is treated with different concentrations of Spirizyme enzyme at 60° C.

Figure 8:
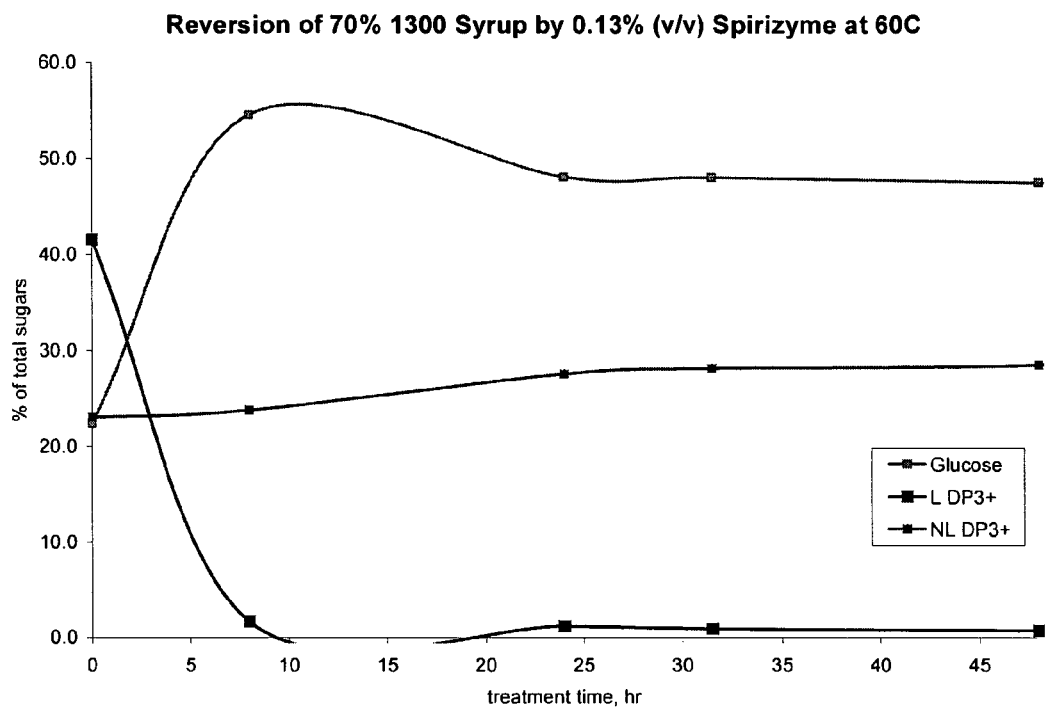
FIG. 8 is a graph of the change over time in the concentrations of certain saccharides when a composition was treated with enzyme in Example 2.

In the treatment of Staley 1300 syrup with glucoamylase, the linear oligomers of DP 3 and greater were rapidly consumed and converted to dextrose. The concentration of these linear oligomers reached its equilibrium of about 1% of total sugars (at 70% syrup concentration, 0.13% Spirizyme at 60° C.) within the first few hours of treatment. (See FIG. 8.) Over a longer period, dextrose concentration slowly decreased, and the concentration of non-linear oligomers slowly increased. The change in concentration of maltose and isomaltose over time mirrors that seen for dextrose reversion (FIG. 7).

Samples from the above experiments were heated above 85° C. for 10-20 minutes to deactivate the enzymes before diluting for ion chromatography analysis. Had the samples been diluted in the presence of active enzyme, they might have been hydrolyzed back to dextrose.

Samples of the reverted syrups were diluted to 20% solids. A portion of each was held in the presence of Spirizyme enzyme at 60° C. and another portion of each was held in the presence of Spirizyme at 40° C. The syrups were sampled over time, and the enzymes in each sample were deactivated as described above.

Figure 9:
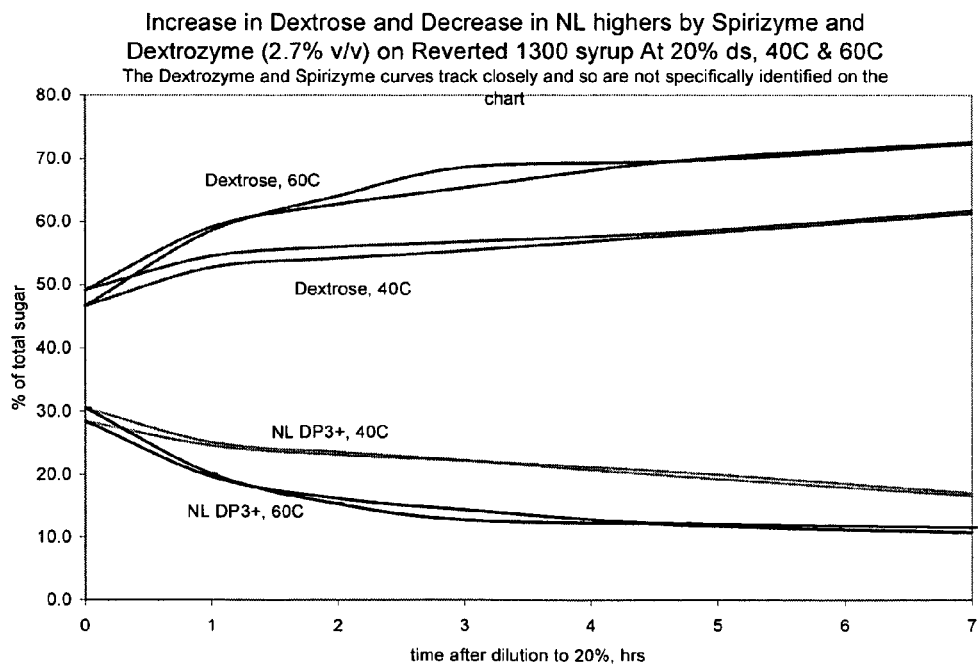
FIG. 9 is a graph of the change over time in the concentrations of certain saccharides when a diluted composition was treated with enzyme in Example 2.

FIG. 9 shows the results. At 60° C., the concentration of nonlinear higher oligomers (DP3 and greater) dropped to half within 3 hours and appeared to plateau at about 11.6% of total sugars by 7 hours. Lower temperature slowed hydrolysis. As FIG. 9 shows, dextrose content increased as a result of hydrolysis. The rate of hydrolysis when two different glucoamylases (Spirizyme and Dextrozyme) were used was identical.

It appears from these experiments that the non-linear oligomers formed through reversion are not immune to hydrolysis by glucoamylase enzymes (or impurities therein). However, it appears that a portion of them is resistant to hydrolysis. At 20% ds the equilibrium between monomer and oligomer is well on the side of monomer. Yet 11.3% DP4+ and 11.6% DP3+ remain after 7 hours at optimum temperature for glucoamylase activity. Compare this with the virtually complete conversion of linear oligomers to dextrose in the same time frame while at much higher solids (70% ds) and half the glucoamylase content, illustrated in FIG. 8. It would appear that, while glucoamylase enzymes can hydrolyze non-linear oligomers, the hydrolysis is not rapid, and may not go to complete conversion. We propose that the digestive enzymes in the human gut will have similarly reduced activity towards these compounds.

Table 3 shows the change in concentration of all sugar species when reverted syrup was diluted to 20% ds at 60° C. in the presence of active Spirizyme enzyme Regardless of starting sugar distribution or degree of conversion, all corn syrups tested were converted to a comparable sugar distribution by glucoamylase if treated at comparable syrup concentrations.

From these experiments, it appears that during the enzymatic reversion of corn syrup, linear oligomers are rapidly hydrolyzed to dextrose. Over longer times and at high syrup concentrations the dextrose is consumed as non-linear oligomers are formed. The production of non-linear oligomers is at least partially reversible, as evidenced by their hydrolysis by glucoamylase at lower syrup solids. Thus, when the reverted syrups are diluted before deactivating the glucoamylase, a portion of, but apparently not all of the oligomers are hydrolyzed back to dextrose monomer. This demonstrates that the formation of non-linear linkages by glucoamylase (or perhaps impurities it contains) is not entirely irreversible "mistakes" by the enzyme.

EXAMPLE 3

Quality of Glucoamylases Impacts Reversion

The amount of enzyme needed to effect the reversion is high relative to typical enzymatic processes. Approximately 1.5% v/v of commonly used glucoamylases (for example, Spirizyme Plus FG and Dextrozyme DX 1.5X, supplied by Novozymes) are needed to reach 80% of equilibrium reversion in 24 hrs at 60-75° C. It should be noted that enzyme manufacturers have made great strides in reducing the tendency of the glucoamylase to form reversion products—improvements driven by the consumers of these enzymes—the manufacturers of corn syrup—for which reversion products are a bane. It is our belief that the enzymes from the 1950s would be much more efficient for forming these non-linear oligomer syrups than current glucoamylases.

Figure 10:
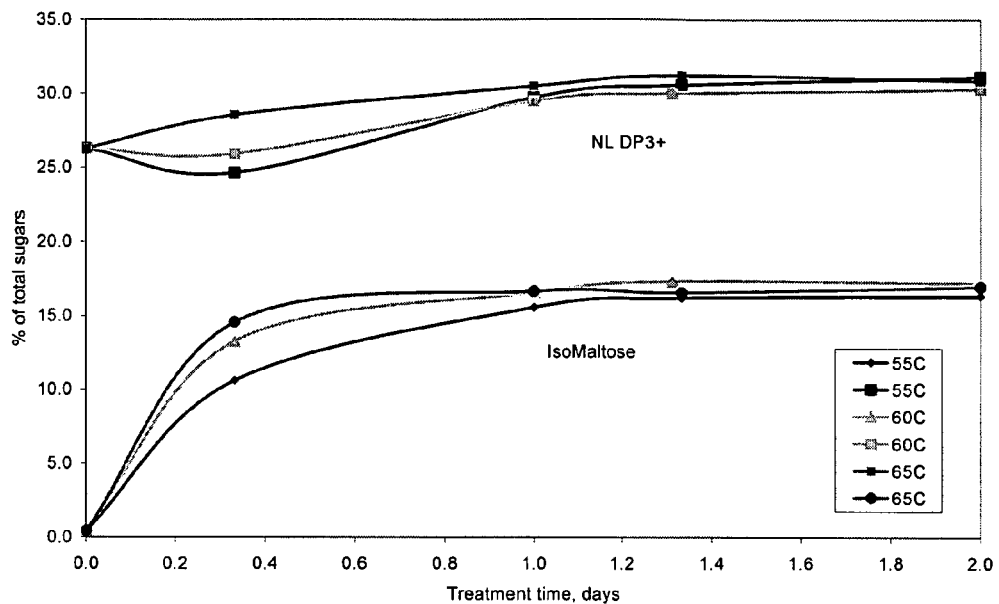
FIG. 10 is a graph of the effect of temperature on the formation of certain saccharides as a result of enzyme treatment in Example 3.
Figure 11:
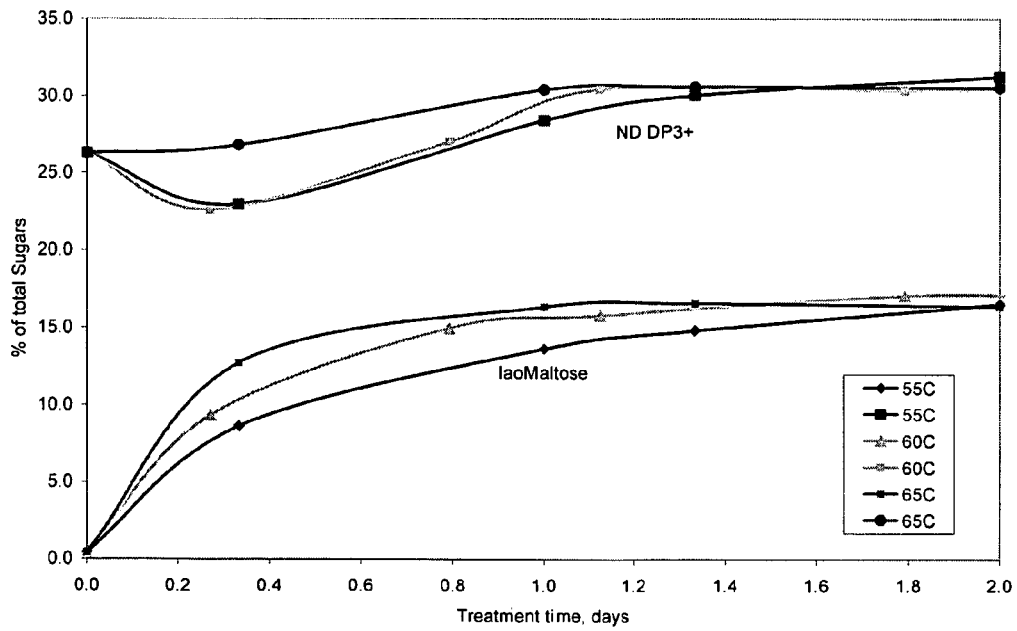
FIG. 11 is a graph of the effect of temperature on the formation of certain saccharides as a result of another enzyme treatment in Example 3.

Lending support to the concept that "impurities" still in these commercial glucoamylases may be responsible for the reversion products in the experiments reported here is the fact that, while Novozymes reports the optimum temperature for activity for both Spirizyme and Dextrozyme to be 59-61° C., the rate of generation of reversion products increases when temperature is increased from 60 to 65° C. FIGS. 10 and 11 show the rate of formation of isomaltose and non-linear oligomers of DP 3 and greater (NL DP3+), as a function of temperature, for Spirizyme and Dextrozyme. The substrate syrup was Staley 1300, and the amount of enzyme used was 2.7% v/v.

TABLE 3

| hr | % of total sugars | | | | | | | |
|---|---|---|---|---|---|---|---|---|
| time | Glucose | Isomaltose | Maltose | Panose | Maltoriose | L DP3+ | NL DP3+ | NL DP4+ |
| 0 | 46.7 | 16.8 | 4.5 | 2.4 | 0.3 | 1.0 | 30.5 | 28.1 |
| 1 | 58.6 | 18.1 | 2.0 | 0.6 | 0.1 | 0.6 | 20.1 | 19.5 |
| 2 | 64.0 | 17.0 | 2.3 | 0.5 | 0.1 | 0.5 | 15.3 | 14.9 |
| 3 | 68.6 | 15.3 | 2.1 | 0.4 | 0.1 | 0.4 | 12.8 | 12.4 |
| 4.75 | 69.6 | 14.7 | 2.1 | 0.3 | 0.1 | 0.5 | 12.2 | 11.9 |
| 7 | 72.3 | 13.0 | 1.9 | 0.3 | 0.1 | 0.5 | 11.6 | 11.3 |

("L DP3+" refers to linear oligomers having a degree of polymerizaion of three or more. "NL DP3+" refers to nonlinear oligomers having a degree of polymerization of three or more. "NL DP4+" refers to nonlinear oligomers having a degree of polymerization of four or more.)

EXAMPLE 4

Acid-Catalyzed Restructuring of Corn Syrup to Form Non-Linear Oligomers

Staley 1300 syrup was diluted 1:4 with deionized water to facilitate pH determinations. The amount of acid (HCl or $H_2SO_4$) to drop syrup pH to the pH target was determined. In one experiment, 10% Krystar crystalline fructose was added to the syrup prior to acid treatment.

Staley 1300 syrup was heated to approximately 60° C. in 50 ml screw-cap centrifuge tubes in a shaking water bath. The pre-determined amount of acid needed to reach target pH was added to the syrup. The syrup tubes were shaken vigorously to uniformly distribute the acid. The tubes were returned to the water bath, and bath temperature adjusted as needed. Treatments were performed at 60, 70, and 80° C., and at pHs of 1.2, 1.8 and 2.3. To monitor the progress of the reactions, portions of the syrup were removed from tubes and neutralized by adding a caustic solution.

The caustic solutions were prepared such that a volume of caustic solution was sufficient to neutralize an equal volume of acidified syrup. Approximately 80% of this volume was added all at once, which diluted the syrup sufficiently for pH measurement. Additional caustic solution was added dropwise until pH reached >5.0 (and preferably no greater than 6.5).

The syrup solutions were analyzed using ion chromatography. In addition to a RSO Oligosaccharide column from Phenomenex, some samples were also analyzed using a Dionex CarboPac PA200 column.

The first acid condensation reaction on Staley 1300 syrup was at pH 2.3 with sulfuric acid, at 60° C. The proportion of linear oligomers decreased, and non-linear oligomers increased.

Figure 12:
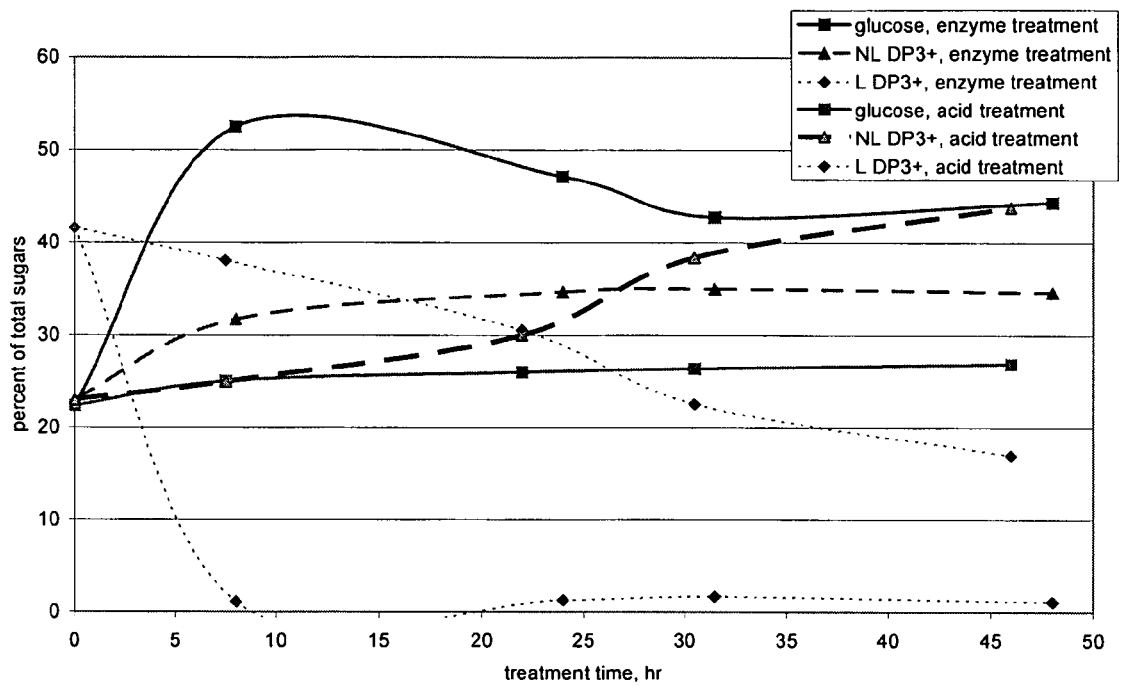
FIG. 12 is a graph comparing the changes in saccharide distribution when a composition was treated by acid or by enzyme in Example 4.

FIG. 12 compares the changes in sugar distributions in Staley 1300 syrup caused by acid treatment and glucoamylase treatment (both at 60° C.). It can be seen that the processes proceed differently. Spirizyme glucoamylase consumes linear oligomers very rapidly, generating dextrose. With Staley 1300 syrup, the concentration of linear oligomers of DP3 and greater drops from approximately 42% of total sugars to its equilibrium value of approximately 1% within hours of contact with the enzyme. Over a longer period, a portion of the dextrose is converted to non-linear oligomers. The concentration of non-linear DP3 and higher (DP3+) increases over about 30 hours (under the conditions of this enzyme treatment).

In contrast, on contact with acid, linear oligomers are consumed and non-linear oligomers formed at comparable rates. Dextrose concentration increases very slowly over the course of the treatment.

In a parallel experiment, 10% dry fructose was added to Staley 1300 syrup, so that the final syrup solids concentration was approximately 90%. It was treated to the same pH, temperature and time as the Staley 1300 syrup by itself. While the Staley 1300 syrup developed color over the course of the treatment, the fructose-containing syrup turned coffee-colored almost immediately. IC analysis of samples pulled from it showed the rate of linear oligomers reduction, and non-linear oligomers generation, comparable to the acid-treated syrup by itself. Fructose content was not significantly altered.

A second round of acid treatments was conducted in which Staley 1300 syrup was adjusted to 1.2 and 1.8 pH with HCl. Each pH treatment was run at temperatures of 70° C. and 80° C. All syrups generated significant color over the course of the treatments. The extent of color increased with decreasing pH, increasing temperature and increasing time. At the extreme, darkly-colored insoluble components formed.

Figure 13:
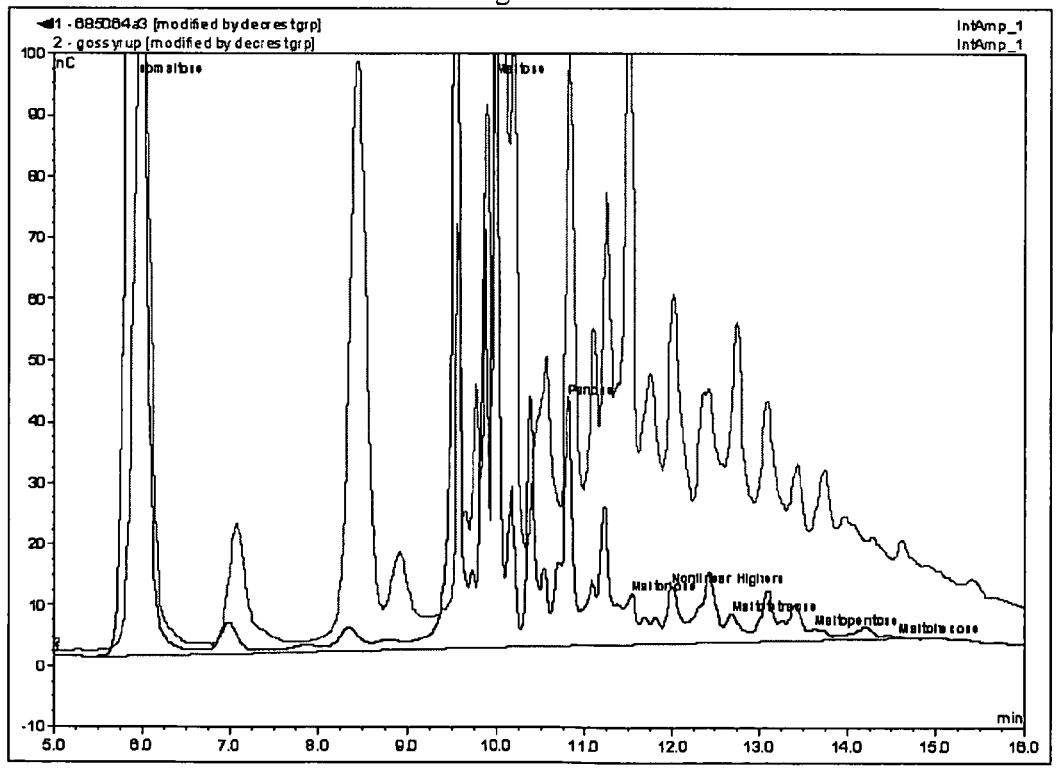
FIG. 13 shows an analysis of a syrup treated with acid in Example 4.

As FIG. 13 illustrates, the product of acid-treated syrup is a very broad distribution of sugar oligomers. It also shows a much higher concentration of oligomers of DP3 than the enzyme reverted syrup. Also, the acid-treated syrup contains sugars which do not appear in the enzyme-treated syrup. This is expected since the acid-catalyzed condensations can occur between any two hydroxyl groups, whereas enzymatic condensations are typically very specific in how two sugar units are joined together.

Figure 14:
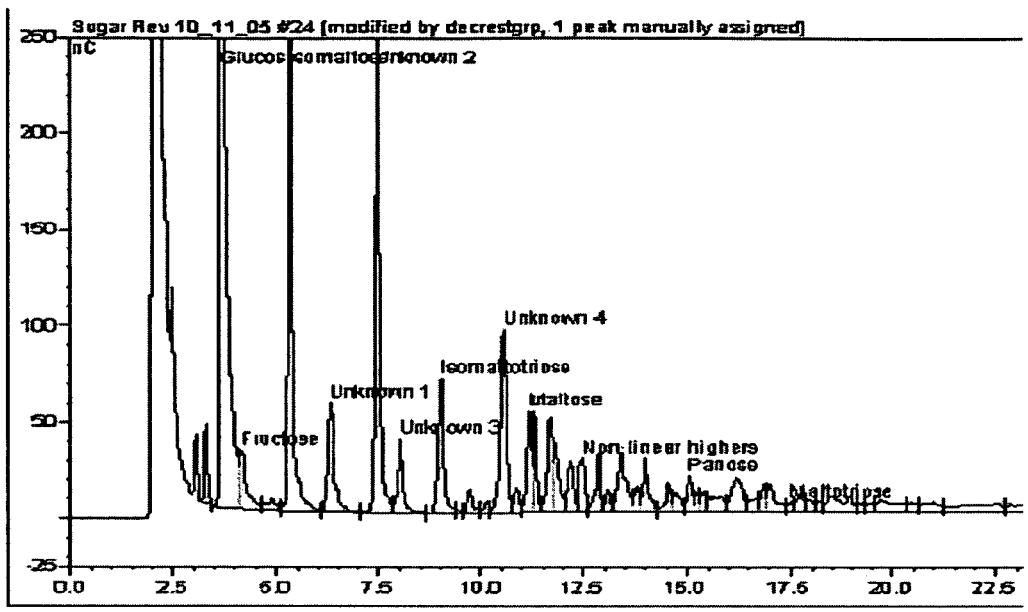
FIG. 14 shows a chromatographic analysis of a syrup treated with acid in Example 4.

A Dionex CarboPac PA200 column was used for ion chromatographic separation of the sugars. FIG. 14 shows a chromatographic trace of an acid-treated syrup resolved by this column. It clearly shows four components in the DP2-3 range that elute separately from maltose, isomaltose, maltotriose and panose. (These four all elute before maltose.) It also shows a number of peaks for unidentified higher oligomers.

Table 4 below shows changes in sugar distribution over time for these four lower-pH, higher-temperature treatments, using the PA200 column. (The last column in the table shows the amount of the "unknown 1-4" peaks, and is not included in the NL DP3+).

TABLE 4

| | C. | hr | | % of total sugars | | | |
|---|---|---|---|---|---|---|---|
| pH | temp | time | color | Glucose | NL DP3+ | L DP3+ | NL DP2-3? |
| 1.8 | 70 | 0 | white | 22 | 23 | 42 | 0 |
| 1.8 | 70 | 4 | white | 27 | 27 | 28 | 1.7 |
| 1.8 | 70 | 8 | white | 28 | 29 | 25 | 2.8 |
| 1.8 | 70 | 24 | white | 34 | 30 | 13 | 7.3 |
| 1.8 | 70 | 48 | tan | 37 | 30 | 4.7 | 14 |
| 1.2 | 70 | 0 | white | 22 | 23 | 42 | 0 |
| 1.2 | 70 | 4 | white | 33 | 30 | 15 | 5.9 |
| 1.2 | 70 | 8 | tan | 36 | 30 | 6.6 | 12 |
| 1.2 | 70 | 24 | tea | 36 | 30 | 0.5 | 20 |
| 1.2 | 70 | 48 | coffee | 35 | 29 | 0.3 | 21 |
| 1.8 | 80 | 0 | white | 22 | 23 | 42 | 0 |
| 1.8 | 80 | 4 | white | 39 | 28 | 1.6 | 18 |
| 1.8 | 80 | 8 | tan | 36 | 29 | 0.7 | 21 |
| 1.8 | 80 | 24 | tea | 35 | 30 | 0.5 | 20 |
| 1.8 | 80 | 48 | coffee | 35 | 29 | 0.4 | 20 |
| 1.2 | 80 | 0 | white | 22 | 23 | 42 | 0 |
| 1.2 | 80 | 4 | tan | 29 | 33 | 18 | 4.5 |
| 1.2 | 80 | 8 | tea | 32 | 32 | 11 | 8.6 |
| 1.2 | 80 | 24 | coffee + insol | 37 | 31 | 0.5 | 18 |
| 1.2 | 80 | 48 | coffee + insol | 33 | 32 | 0.2 | 21 |

EXAMPLE 5

Enzyme Reversion—High Sugar

Approximately 35 gal of 43 DE corn syrup at 80% dry solids (Staley 1300) with an additional 5 gal of deionized water was slowly agitated in a tank and heated to a temperature of 60° C. About 1.6 gal of Spirizyme Plus FG enzyme was added to the syrup slowly and with good agitation. After 24 hours at 60° C., the syrup was heated to 85° C. and held for 20 minutes. The syrup was then diluted from 70% to 20% dry solids concentration by adding 100 gal water. The sugar solution was subjected to nanofiltration using a Desal NF3840C 30D nanofiltration cartridge at about 500 psi of pressure and at a temperature of 55-60° C. Fresh diafiltration water was added to maintain permeate flux in the range of 2 to 10 LMH. Filtration continued until the retentate contained less than 5% dextrose (dsb) by combination of Karl Fisher and YSI dextrose analysis. The nanofiltration retentate was treated with 1% activated carbon on a dry solids basis. Next, the carbon was removed by filtration and the filtrate evaporated to 80.2% ds.

A saccharide analysis of the final product was performed by HPAE-PAD chromatography, and the results are shown in Table 5.

TABLE 5

| Component | Wt % d.s.b. |
| --- | --- |
| dextrose | 1.1% |
| fructose | 0.1% |
| isomaltose | 27.7% |
| maltose | 5.2% |
| maltotriose | 0.3% |
| panose | 3.2% |
| linear higher saccharides | 3.3% |
| nonlinear higher saccharides | 59.1% |

("Higher saccharides" in the above table means oligomers having a DP of three or more.)

EXAMPLE 6

Enzyme Reversion—Low Sugar

Approximately 35 gal of 43 DE corn syrup at 80% dry solids (Staley 1300) with an additional 5 gal of deionized water was slowly agitated in a tank and heated to a temperature of 60° C. About 1.6 gal of Spirizyme Plus FG enzyme was added to the syrup slowly and with good agitation. After 24 hours at 60° C., the syrup was heated to 85° C. and held for 20 minutes. The syrup was then diluted from 70% to 20% dry solids concentration by adding 100 gal water. The sugar solution was subjected to ultrafiltration using a Desal UF-1 3840C 50D ultrafiltration cartridge at about 400 psi of pressure and at a temperature of 55-60° C. Fresh diafiltration water was added to maintain permeate flux in the range of 10 to 20 LMH. Filtration continued until the retentate contained less than 1% dextrose (dsb) by combination of Karl Fisher and YSI dextrose analysis. The ultrafiltration retentate was treated with 1% activated carbon on a dry solids basis. Next, the carbon was removed by filtration and the filtrate evaporated to 73.4% ds.

A saccharide analysis of the final product was performed by HPAE-PAD chromatography, and the results are shown in Table 6.

TABLE 6

| Component | Wt % d.s.b. |
| --- | --- |
| dextrose | 1.0% |
| fructose | 0.1% |
| isomaltose | 6.0% |
| maltose | 7.5% |
| maltotriose | 0.4% |
| panose | 4.4% |
| linear higher saccharides | 7.2% |
| nonlinear higher saccharides | 73.3% |

EXAMPLE 7

Enzyme Reversion—High Isomaltose

The syrup from Example 5 was subjected to ultrafiltration using a Desal UF-1 3840C 50D ultrafiltration cartridge at about 400 psi of pressure and at a temperature of 55-60° C. The permeate from this operation was then subjected to nanofiltration using a Desal NF3840C 30D nanofiltration cartridge at about 500 psi of pressure and at a temperature of 55-60° C. Fresh diafiltration water was added to maintain permeate flux in the range of 2 to 10 LMH. Filtration continued until the retentate contained less than 5% dextrose (dsb) by combination of Karl Fisher and YSI dextrose analysis. The nanofiltration retentate was treated with 1% activated carbon on a dry solids basis. Next, the carbon was removed by filtration and the filtrate evaporated to 90.2% ds.

A saccharide analysis of the final product was performed by HPAE-PAD chromatography, and the results are shown in Table 7.

TABLE 7

| Component | Wt % d.s.b. |
| --- | --- |
| dextrose | 2.8% |
| fructose | 0.0% |
| isomaltose | 70.8% |
| maltose | 6.5% |
| maltotriose | 0.1% |
| panose | 0.6% |
| linear higher saccharides | 0.0% |
| nonlinear higher saccharides | 19.2% |

EXAMPLE 8

Acid Reversion—Moderately Resistant

Approximately 35 gal of 43 DE corn syrup at 80% dry solids (Staley 1300) was slowly agitated in a tank and heated to a temperature of 80° C. About 4.1 lb 37% hydrochloric acid was added to the syrup slowly and with good agitation. The reaction was maintained at approximately 80% dry solids concentration, as measured by Karl Fischer analysis through periodic additions of water. After 24 hours, heating was discontinued and approximately 35 gal of 0.35% sodium hydroxide solution was added slowly and with good agitation. Next, pH was adjusted to 5.0 and water was added to reach a final sugar concentration of 30% d.s. The sugar solution was subjected to ultrafiltration using a Desal UF-1 ultrafiltration cartridge at about 400 psi of pressure and at a temperature of 55-60 C. Fresh diafiltration water was added to maintain permeate flux in the range of 10 to 20 LMH. Filtration continued until the retentate contained less than 5% dextrose (dsb) by combination of Karl Fisher and YSI dextrose analysis. The ultrafiltration retentate was treated with 2% activated carbon on a dry solids basis. Next, the carbon was removed by filtration and the filtrate evaporated to 71.5% ds.

A saccharide analysis of the final product was performed by HPAE-PAD chromatography, and the results are shown in Table 8.

TABLE 8

| Component | Wt % d.s.b. |
| --- | --- |
| dextrose | 6.4% |
| fructose | 0.1% |
| isomaltose | 1.6% |
| maltose | 3.8% |
| maltotriose | 4.3% |
| panose | 3.8% |
| linear higher saccharides | 25.6% |

TABLE 8-continued

| Component | Wt % d.s.b. |
| --- | --- |
| nonlinear higher saccharides | 54.9% |

EXAMPLE 9

Acid Reversion Followed by Hydrogenation

Approximately 35 gal of 63 DE corn syrup at 80% dry solids (SWEETOSE® 4300) was slowly agitated in a tank. Then 37% hydrochloric acid was added slowly with good agitation to give 0.25% (w/w) HCl with respect to syrup dry solids. The mixture was then heated to a temperature of 80° C. The reaction was maintained at approximately 80% dry solids concentration, as measured by Karl Fischer analysis through periodic additions of water. After 16 hours, heating was discontinued and pH was adjusted to 4.5 using 0.35% sodium hydroxide solution. Additional water was added to reach a final sugar concentration of 30% d.s. The sugar solution was subjected to ultrafiltration using a Desal UF-1 ultrafiltration cartridge at about 400 psi of pressure and at a temperature of 55-60° C. Fresh diafiltration water was added to maintain permeate flux in the range of 10 to 20 LMH. Ultrafiltration continued until the retentate contained less than 10% dextrose (dsb) by combination of Karl Fisher and YSI dextrose analysis. The ultrafiltration retentate was subjected to nanofiltration using a Desal NF3840C 30D nanofiltration cartridge at about 500 psi of pressure and at a temperature of 55-60° C. Fresh diafiltration water was added to maintain permeate flux in the range of 2 to 10 LMH. Filtration continued until the retentate contained less than 1% dextrose (dsb) by combination of Karl Fisher and YSI dextrose analysis. The nanofiltration retentate was treated with 1% activated carbon on a dry solids basis. Next, the carbon was removed by filtration and the filtrate evaporated to 73.5% ds.

Dextrose Equivalence (DE) for this product was measured by AOAC method 920.51 (Lane Eynon) and was found to be 21 DE. A saccharide analysis of this product was performed by HPAE-PAD chromatography, and the results are shown in Table 9.

TABLE 9

| Component | Wt % d.s.b. |
| --- | --- |
| dextrose | 1.4% |
| fructose | 0.1% |
| isomaltose | 0.0% |
| maltose | 4.3% |
| sorbitol | 0.0% |
| panose | 6.3% |
| linear higher saccharides | 12.6% |
| nonlinear higher saccharides | 75.2% |

This product was further subjected to hydrogenation reaction conditions. About 1.5 kg of a 43% d.s. solution of the material described in table 9 was introduced into a pressure reactor and 6.45 grams of 5% ruthenium on carbon catalyst was added with stirring to give 0.05% ruthenium (w/w) on syrup dry solids. The reactor was closed, purged with nitrogen gas, and then pressurized with hydrogen gas to a pressure of 600 psi. The reactor was then heated to 120° C. This temperature and a hydrogen pressure of 600-650 psi was maintained for four hours. The reaction vessel was cooled, carefully vented and purged with nitrogen. The reaction product was then filtered through diatomaceous earth to give a clear colorless solution.

Dextrose Equivalence (DE) for this product was measured by AOAC method 920.51 (Lane Eynon) and was found to be 5 DE. A saccharide analysis of this product was performed by HPAE-PAD chromatography, and the results are shown in Table 10.

TABLE 10

| Component | Wt % d.s.b. |
| --- | --- |
| dextrose | 3.1% |
| fructose | 0.2% |
| isomaltose | 0.0% |
| maltose | 5.9% |
| sorbitol | 3.0% |
| panose | 5.6% |
| linear higher saccharides | 9.5% |
| nonlinear higher saccharides | 72.7% |

EXAMPLE 10

Englyst Digestion Assay

The product materials from Examples 5, 6 and 8, were tested for digestibility using an Englyst assay. About 600 mg of carbohydrate d.s.b. was added to 20 mL of 0.1 M sodium acetate buffer in a test tube. The contents were mixed and then heated to about 92° C. for 30 minutes, then cooled to 37° C. Then 5 mL of enzyme solution was added to the test tube and it was agitated by shaking in a water bath at 37° C. Small samples were removed at both 20 min and 120 min. The enzyme was inactivated; the samples were filtered and measured for digestibility using a dextrose test from YSI Inc. A 10 DE maltodextrin (STAR-DRI 10), known to be very digestible, was also tested as a comparison. The results of the digestibility assay and a saccharide analysis are shown in Table 11. A 10 DE maltodextrin is included in Table 5 for comparison. All percentages in Table 11 are on a d.s.b.

TABLE 11

| material | % rapidly digestible | % slowly digestible | % resistant | % non-linear highers (by HPAE) |
| --- | --- | --- | --- | --- |
| Example 5 | 4.2 | 10.2 | 85.6 | 59.1 |
| Example 6 | 5.2 | 10.0 | 84.8 | 73.3 |
| Example 8 | 24.8 | 5.5 | 69.8 | 54.9 |
| 10 DE maltodextrin | 89.7 | 3.4 | 7.0 | 13.7 |

("Highers" in Table 11 refers to oligomers having a degree of polymerization of three or more.)

There was an excellent correlation ($R^2=0.95$) between the percentage of non-linear highers in the material and the percentage of the material that was resistant to digestion.

EXAMPLE 11

Hard Candy, Lemon Flavored 980 grams (d.s.b.) of Example 5 (Enzyme Reversion—High Sugar) was added to a pot and cooked on a stove to an internal temperature of 300° F. Next, 15 grams of citric acid and 1.2 grams of sucralose were added with stirring. Then, yellow color and lemon flavor were added and the mixture was poured into candy moulds. The hard candy was formed upon cooling to room temperature.

EXAMPLE 12

Jelly Candy, Grape Flavored 840 grams of Example 6 (Enzyme Reversion—Low Sugar) was added to a mixing bowl. Purple color and grape flavor was added to taste. Next, 160 grams of MiraThik 468 instant starch was added in portions with moderately vigorous mixing. The jelly candy was formed after cooling to room temperature over 20 minutes.

EXAMPLE 13

Yogurt 900 grams of milk (2% fat) was added to a pot on a stove. Next 80 grams (d.s.b) of Example 8 (Acid Reversion—Moderately Resistant) was added with stirring. Then the mixture was heated to a target temperature of 150° F. As the mixture was heating, 20 grams of Rezista 682 starch was added in portions with mixing. After the mixture reached an internal temperature of 150° F., it was held for five minutes, then passed through a two stage homogenizer (1500/500 psi). The product was next pasteurized at 190° F. for 5 minutes. Then the mixture was cooled to 90° F. and inoculated with active yogurt cultures. The incubation was allowed to continue until the yogurt reached a pH of 4.5, then it was refrigerated prior to consumption.

The preceding description illustrates certain specific embodiments of the invention. It is not an exhaustive list of all possible embodiments of the invention. A person of ordinary skill in this field will recognize that modifications can be made to the specific embodiments described herein which will remain within the scope of the following claims.

What is claimed is:

1. A process for preparing saccharide oligomers, comprising:
heating an aqueous feed composition that comprises at least one monosaccharide or linear saccharide oligomer, and that has a solids concentration of at least about 70% by weight, to a temperature of at least about 40° C.; and
contacting the feed composition with at least one catalyst that accelerates the rate of cleavage or formation of glucosyl bonds for a time sufficient to cause formation of non-linear saccharide oligomers, wherein a product composition is produced that contains a higher concentration of non-linear saccharide oligomers than linear saccharide oligomers; wherein the product composition comprises non-linear saccharide oligomers having a degree of polymerization of at least three in a concentration of at least about 20% by weight on a dry solids basis.

2. The process of claim 1, wherein the aqueous feed composition comprises at least one monosaccharide and at least one linear saccharide oligomer.

3. The process of claim 1, wherein the aqueous feed composition is a dextrose syrup, a corn syrup, or a solution of maltodextrin.

4. The process of claim 1, wherein at least about 50% by weight on a dry solids basis of the product composition is slowly digestible.

5. The process of claim 1, wherein the feed composition is contacted with the at least one catalyst for at least about five hours.

6. The process of claim 1, wherein the feed composition is contacted with the at least one catalyst for about 15-100 hours.

7. The process of claim 1, wherein the at least one catalyst is an enzyme that accelerates the rate of cleavage or formation of glucosyl bonds.

8. The process of claim 7, wherein the enzyme accelerates the rate of cleavage of alpha 1-2, 1-3, 1-4, or 1-6 glucosyl bonds to form dextrose residues.

9. The process of claim 7, wherein the enzyme is a glucoamylase enzyme composition.

10. The process of claim 7, wherein the amount of enzyme is about 0.5-2.5% by volume of the feed composition.

11. The process of claim 7, wherein the feed composition is maintained at about 55-75° C. during the contacting with the enzyme.

12. The process of claim 11, wherein the feed composition is maintained at about 60-65° C. during the contacting with the enzyme.

13. The process of claim 7, wherein the feed composition is contacted with the enzyme for about 20-100 hours prior to inactivation of the enzyme.

14. The process of claim 13, wherein the feed composition is contacted with the enzyme for about 50-100 hours prior to inactivation of the enzyme.

15. The process of claim 1, wherein the at least one catalyst is an acid.

16. The process of claim 15, wherein the acid is hydrochloric acid, sulfuric acid, phosphoric acid, or a combination thereof.

17. The process of claim 15, wherein acid is added to the feed composition in an amount sufficient to make the pH of the feed composition no greater than about 4.

18. The process of claim 15, wherein acid is added to the feed composition in an amount sufficient to make the pH of the feed composition about 1.0-2.5.

19. The process of claim 15, wherein the feed composition has a solids concentration of about 70-90% and is maintained at a temperature of about 70-90° C. during the contacting with the acid.

20. The process of claim 15, wherein the solids concentration of the feed composition is at least about 80% by weight, the acid is added to the feed composition in an amount sufficient to make the pH of the composition about 1.8, and the feed composition is maintained at a temperature of at least about 80° C. for about 4-24 hours after it is contacted with the acid.

21. The process of claim 15, wherein the solids concentration of the feed composition is about 90-100% by weight, and the feed composition is maintained at a temperature of at least about 149° C. for about 0.1-15 minutes after it is contacted with the acid.

22. The process of claim 21, wherein the acid comprises a combination of phosphoric and hydrochloric acid.

23. The process of claim 1, wherein the feed composition comprises at least about 75% solids by weight.

24. The process of claim 23, wherein the feed composition comprises about 75-90% solids by weight.

25. The process of claim 1, wherein the product composition comprises non-linear saccharide oligomers having a degree of polymerization of at least three in a concentration of at least about 25% by weight on a dry solids basis.

26. The process of claim 25, wherein the product composition comprises non-linear saccharide oligomers having a degree of polymerization of at least three in a concentration of at least about 30% by weight on a dry solids basis.

27. The process of claim 26, wherein the product composition comprises non-linear saccharide oligomers having a degree of polymerization of at least three in a concentration of at least about 50% by weight on a dry solids basis.

28. The process of claim 1, wherein the concentration of non-linear saccharide oligomers in the product composition is at least twice as high as the concentration of linear saccharide oligomers.

29. The process of claim 1, wherein the product composition comprises a minor amount of residual monosaccharides, and wherein the process further comprises removing at least some residual monosaccharides from the product composition by membrane filtration, chromatographic fractionation, or digestion via fermentation.

30. The process of claim 1, wherein the at least one catalyst that accelerates the rate of cleavage or formation of glucosyl bonds is enzyme, and the product composition is subsequently contacted with an acid that accelerates the rate of cleavage or formation of glucosyl bonds.

31. The process of claim 1, wherein the at least one catalyst that accelerates the rate of cleavage or formation of glucosyl bonds is acid, and the product composition is subsequently contacted with an enzyme that accelerates the rate of cleavage or formation of glucosyl bonds.

32. The process of claim 1, further comprising hydrogenating the product composition.

33. The process of claim 32, wherein the hydrogenating decolorizes the product composition but does not substantially change its dextrose equivalence.

34. The process of claim 1, further comprising hydrolyzing a maltodextrin to form a hydrolyzed saccharide solution and concentrating the hydrolyzed saccharide solution to at least about 70% dry solids to form the feed composition.

35. The process of claim 34, wherein the concentrating and the contacting of the feed composition with the at least one catalyst occur simultaneously.

36. The process of claim 35, wherein the concentrating occurs prior to the contacting of the feed composition with the at least one catalyst.

* * * * *